United States Patent [19]

Bohm

[11] Patent Number: 4,857,335

[45] Date of Patent: Aug. 15, 1989

[54] LIQUID CONTROLLED RELEASE FORMULATIONS AND METHOD OF PRODUCING SAME VIA MULTIPLE EMULSION PROCESS

[75] Inventor: Howard A. Bohm, Richmond, Va.

[73] Assignee: Lim Technology Laboratories, Inc., Richmond, Va.

[21] Appl. No.: 31,047

[22] Filed: Mar. 27, 1987

[51] Int. Cl.$^4$ .............................................. A61K 9/66
[52] U.S. Cl. .................................... 424/455; 424/440; 514/937
[58] Field of Search ............................ 424/455; 514/2

[56] References Cited

U.S. PATENT DOCUMENTS 4,652,441 3/1987 Okada .................................. 424/49
4,711,782 12/1987 Okada ................................ 424/455

Primary Examiner—Thurman K. Page
Assistant Examiner—P. Prater
Attorney, Agent, or Firm—Burns, Doane, Swecker & Mathis

[57] ABSTRACT

Liquid, controlled release formulations are provided by emulsifying an aqueous active ingredient-polymer complex, an organic solution of a film-forming polymer and an organic solvent, and a surfactant to form a first emulsion. An aqueous solution of a surfactant is emulsified with the first emulsion to produce a second emulsion and the organic solvent is subsequently removed to produce a liquid controlled release formulation. The formulation so produced includes an aqueous dispersion of microcapsules having permeable shells of the film-forming polymer and aqueous cores of the aqueous active ingredient-polymer complex.

20 Claims, 7 Drawing Sheets

LIQUID CONTROLLED RELEASE FORMULATIONS AND METHOD OF PRODUCING SAME VIA MULTIPLE EMULSION PROCESS

BACKGROUND OF THE INVENTION

The present invention relates to liquid controlled release formulations useful as delivery systems. In particular, the present invention relates to microcapsular controlled release formulations in liquid dosage forms which are prepared via a multiple emulsion process.

Controlled release formulations, especially for the administration of therapeutically active materials, are well known in the art. Solid controlled release formulations are most common. These solid controlled release formulations can be in tablet form and often comprise a core of a therapeutically active material which is coated with varying thicknesses of inactive digestible materials. Other solid controlled release formulations comprise alternating layers of therapeutically active materials and inactive digestible materials.

Controlled release formulations in liquid form are not as common in the art as solid controlled release formulations. A basic kind of liquid controlled release formulation comprises a suspension of an ion exchange resin in finely divided form complexed with a pharmaceutical, such as that disclosed in U.S. Pat. No. 2,990,332. This kind of formulation provides only a minor delay in release. Still further, these finely divided ion exchange resins are generally not available in the specific particle sizes needed to achieve a specific desired release rate. Even further, such formulations have additional disadvantages in that they have large particle sizes and thus are not suitable for injectable routes of administration. Further, they are not storage stable and/or have only a short shelf-life due to limited stability. Moreover, these suspensions must be well-mixed prior to administration. Particular problems may arise upon transfer of unmixed suspensions to another container, since a homogeneous sample would not be present in the new container and accurate dosing would now be an impossibility.

Still another disadvantage of these suspensions is that they are gritty to the taste. Many of these disadvantages tend to lower patient compliance, and irregular blood levels of the desired drug may result.

Various other liquid controlled release formulations have been suggested by the art. PCT Application WO No. 85/03000 describes as sustained release liquid dosage formulation produced by coating a pre-made solid controlled release dosage form with a dual coating and subsequently dispersing the resulting dosage forms in a liquid carrier. Disadvantages inherent with this method include the requirement for a pre-made controlled release form, thus these formulations are not prepared in situ and they require at least two further processing steps to achieve a liquid dosage form.

Another method for producing liquid controlled release formulations is disclosed in U.S. Pat. No. 4,205,060. That method involves first forming microcapsules which are recovered as a dry powder and subsequently dispersing the powder in a liquid vehicle. Again, however, the final product of this method is a dry powder, thereby requiring further processing to arrive at a liquid formulation. Further, a larger particle size, on the order of 20-30 microns, oftentimes results, thus lending a gritty texture to the final product.

An additional method is disclosed in U.S. Pat. No. 5,221,778, wherein a substantial portion of drug-resin complexes are treated with a solvating agent and are then provided with a water-permeable diffusion barrier coating. This method, however, also results in dry particles and additionally requires a separate coating step. The coating may be achieved by employing an air suspension or fluidized bed coating apparatus. Thus, the search for an improved liquid controlled release formulation is still sought by the art.

SUMMARY OF THE INVENTION

Accordingly, the present invention provides a liquid controlled release formulation and a method for preparing the same that overcomes the disadvantages present in the liquid controlled release formulations currently offered by the art.

The present invention provides a liquid controlled release formulation comprising an aqueous vehicle having dispersed therein permeable microcapsules each having a shell of a copolymer of acrylic and methacrylic acid esters with pendant quaternary ammonium groups and an aqueous core having complexes of an active ingredient and a complex-forming polymer. In one embodiment, the controlled release formulation of the present invention comprises a mixture of microcapsules having different release characteristics. Such a combination of microcapsules can be formulated to provide release characteristics approximating zero order release. In another embodiment of the present invention, the controlled release formulation of the present invention comprises a mixture of at least two different active ingredient-polymer complexes each separately encapsulated. Alternatively, two or more active ingredients can be encapsulated within the same microcapsule.

By the present invention, a liquid controlled release formulation is provided which can be administered orally or by various parenteral methods, such as by injection (intravenous, intramuscular, subcutaneous, intraperitoneal or the like), as an aerosol for inhalation, topically, as eye drops, ear drops, topical carriers, application as a poultice, and the like. The present invention is also particularly useful for administering target drugs, that is, drugs which are targeted for release at a specific site, and for cancer chemotherapy.

The present invention also provides a method for preparing a liquid controlled release dosage formulation, comprising the steps of preparing an aqueous solution of an active ingredient and a complex-forming polymer to produce active ingredient-polymer complexes, preparing an organic solution of a film-forming polymer in an organic solvent, adding a first surfactant to the aqueous solution or to the organic solution or to both solutions, emulsifying the aqueous solution with the organic solution to produce an aqueous-organic first emulsion, preparing an aqueous solution of a second surfactant, emulsifying the aqueous solution of the second surfactant with the first emulsion to produce an aqueous-organic-aqueous second emulsion, and removing the organic solvent from the second emulsion to produce an aqueous dispersion of microcapsules each having a permeable polymeric shell of the film-forming polymer encapsulating an aqueous core of active ingredient-polymer complexes. The microcapsular dispersions are generally in the form of aqueous suspensions.

It is preferred that the complex forming polymer comprise a copolymer of acrylic and methacrylic acid esters having free acid groups or a copolymer of dimethylaminoethyl methacrylates and neutral methacrylic acid esters. It is also preferred that the film-forming polymer, the one which forms the permeable polymeric shell, comprise a copolymer of acrylic and methacrylic acid esters having pendant quaternary ammonium groups. The first surfactant, or the second surfactant, or both, preferably comprise fatty acid partial esters of sorbitol anhydrides.

The active ingredient can be any pharmaceutical, vitamin, mineral, hormone, other biologically active substance or mixture thereof, that is capable of forming a complex in aqueous solution.

Advantages of formulations as provided by the present invention include the administration of drugs and the like to individuals who have difficulty swallowing tablets or capsules, especially for young children and elderly patients. An additional advantage of the present invention is that the liquid controlled release formulations so produced are formed in situ, thus obviating the need for additional processing steps to achieve an administrable liquid dosage form. Still another advantage of the present invention is that the formulations produced provide a controlled release of the active ingredient or ingredients over an extended period of time, such as ten to twenty hours or even longer. The controlled release formulations of the present invention are also suitable for use in an injectable dosage form.

DETAILED DESCRIPTION OF THE INVENTION

Figure 1:
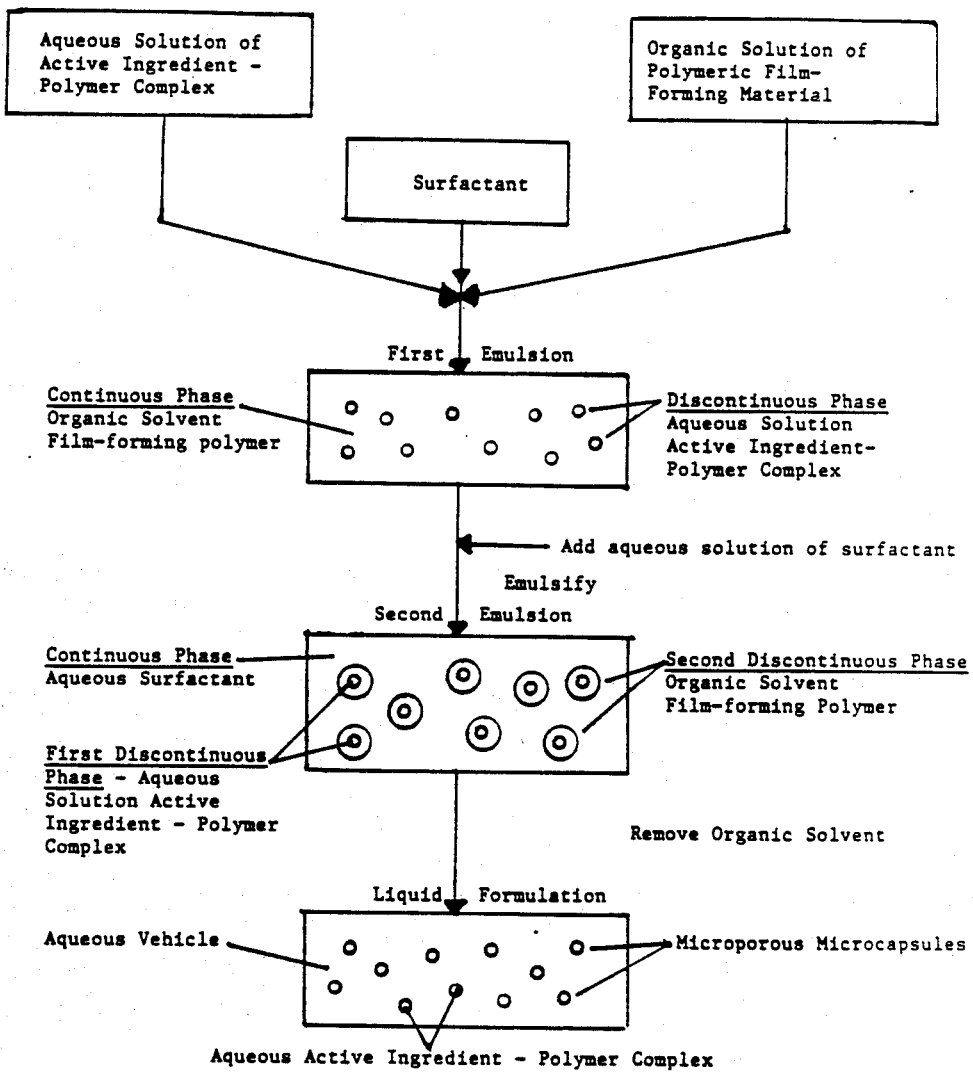
FIG. 1 is a graphic representation of the multiple emulsion process of the present invention for producing a liquid controlled release formulation.

This invention provides a liquid controlled release dosage formulation and a method for producing the same. The present controlled release formulation is particularly suitable for the delivery of therapeutic doses of a wide number of products, especially pharmaceuticals including the topical application of medicaments or the administration of vaccines. The subject controlled release formulation is also useful for the controlled delivery of pesticides such as insecticides, nematocides and fungicides, herbicides, water treatment chemicals, and the like. These formulations are prepared, generally, via a multiple emulsion encapsulation process. The result of this preparation is an aqueous dispersion of microcapsules each having a permeable polymeric film surrounding an aqueous solution of complexes of an active ingredient and a complex-forming polymer.

The dispersion of microcapsules resulting from the multiple emulsion process is useful as an oral liquid controlled release formulation. Such formulations are therapeutically useful for administering oral dosages which have controlled release characteristics. As a practical matter, liquid dosages are especially useful for administering to children, older patients, and others who have difficulty or are not comfortable with swallowing tablets or capsules. Tablets and capsules may also be developed which include the liquid controlled release dosage form described herein. Liquid controlled release formulations of the present invention can also be administered intravenously, such as through a 27 gauge syringe needle; subcutaneously; intramuscularly; intraperitonally. Administration by an infusion pump is also envisioned. Additionally, the present formulations are useful for other routes of parenteral administration, including, but not limited to, aerosols for inhalation, eye drops, ear drops, topical carriers, and application as a poultice.

The present invention thus provides an aqueous dispersion of permeable microcapsules having aqueous cores comprising complexes of an active ingredient and a complex-forming polymer. The active ingredient can be useful for any of the applications mentioned above. Exemplary categories of active ingredients include pharmaceuticals, vitamins, minerals, hormones, other biologically active substances, mixtures thereof, and the like. Preferred pharmaceuticals or drugs include diphenhydramine, propranolol, chlorpheniramine, chlordiazepoxide, oxypranolol, phenylpropranolamine, dextromethorphan, aspirin, indomethacin, valproic acid, pilocarpine, and the like. The sole criterion for the active ingredient is that it must be capable of forming a complex with the complex-forming polymer in aqueous solution. Thus, a wide number of biologically active substances are suitable in the present invention.

Polymers which can form a complex with an active ingredient, that is, biologically active substances, are well known in the art. For example, polymers having acid groups can form complexes with active ingredients having basic groups. Exemplary acid-group containing polymers include polyacrylic acid, water soluble acrylic acid/methacrylic acid copolymers, maleic acid polymers and copolymers (such as maleic acid and vinyl methyl ether), carboxymethylcellulose, polyvinylsulfonic acid, and cellulose acetate polymers such as cellulose acetate phthalate. Preferred acid group containing polymers include anionic copolymers of methacrylic acids and methacrylic acid methyl esters. Especially preferred are those copolymers available from Rohm Pharma under the tradename Eudragit, especially Eudragit L copolymer (degree of esterification 52 mol%, molecular weight of about 250,000) and Eudragit S copolymer (degree of esterification 72 mol %).

Similarly, for an active ingredient having acid groups, such as aspirin, indomethacin, or valproic acid, a polymer having basic groups is used for the complex. Exemplary polymers having basic groups include chitosan and Eudragit E-100 copolymer (tradename of Rohm Pharma), a cationic copolymer of dimethylaminoethyl methacrylate and neutral methacrylic acid ester.

It is preferred that distilled or deionized water is used to obtain the aqueous environment of the present invention. Distilled water is particularly preferred. Preferably, little or no counter ions are present in the water. Small traces of ethanol or other impurities present in the water would have no appreciable effect on the formulations of the present invention.

Polymerized around the aqueous complexes, in the form of permeable microcapsules, is a second polymer which is both water insoluble and is capable of forming a permeable film. Examples of water-insoluble, film-forming polymers include methylcellulose, ethylcellulose and other celluloses, cellulose acetate polymers such as cellulose acetate butyrate, polyvinyl acetates including ethylene vinyl acetate, polyvinyl butyral, and polystyrene ethylene vinyl acetate, polyvinyl alcohol, polyacrylic acid and polymethacrylic acid polymers and copolymers, polystyrene, styrene-butadiene, and the like. Preferred are copolymers synthesized from acrylic and methacrylic acid esters having a low content of quaternary ammonium groups. Especially preferred are copolymers commercially available under the tradenames Eudragit RL and Eudragit RS (a copolymer of trimethylammoniumethylmethacrylate chloride, methacrylic acid methylester, and acrylic acid ethyl ester in a ratio of 5:65:30), available from Rohm Pharma.

Also useful as the film-forming polymers are the Eudragit L and/or S copolymers mentioned above. Microcapsules formed from Eudragit L and/or S copolymers will, in certain physiological environments, break down and release the encapsulated materials.

In final form, the present invention provides an aqueous dispersion of permeable microcapsules of the above-described film-forming polymer surrounding cores of aqueous solutions containing the above-described active ingredient-polymer complexes. The microcapsules produced are on the order of about 0.5 to about 20 microns in size. Preferably, the microcapsules range in size from about 0.5 to about 10 microns. For injectable administration, the microcapsules are preferably about 0.5–10 microns in size; for oral administration, the microcapsules are preferably about 0.5–20 microns in size.

It is readily noted that the process of the present invention allows for the formation of a liquid controlled release formulation in situ. That is, no further significant processing of the product is required before administration. This is a significant advantage over many of the prior art processes. Obviously, it may be desirable to add thickeners, viscosity improvers, flavorants, and other nontoxic pharmaceutical adjuvants to the final liquid controlled release formulation; however, these inert pharmaceutical additives require no major processing effort to incorporate them into the final formulation. Plasticizers, such as dibutyl phthalate or polyethylene glycol (molecular weight of from about 1,000 to about 40,000), can be incorporated into the wall material of the microcapsules, generally in amounts of from about 10 to 20% by weight based on the film-forming polymer.

For use as a therapeutic agent, the liquid controlled release formulations can be administered orally or parenterally. While not desirous of being constrained to any particular theory, it is believed that the release mechanism of the present formulation functions by the permeation of a small ion, such as potassium, sodium, or calcium, into the microcapsule, the subsequent displacement by the permeating ion of the active ingredient from the complex, and the final diffusion of the active ingredient out of the permeable microcapsule. Thus, the small ion is exchanged for the active ingredient. The polymer salt, on the other hand, remains within the microcapsule and cannot exit therefrom. Further, for example, when the present formulation is used for eyedrops, after the active ingredient is released, the microcapsules are designed to break down to avoid irritation of the eye.

The method of the present invention for preparing the microcapsular dispersion comprises what is termed herein as a multiple emulsion process.

The first step of the present method comprises forming two solutions. One solution is aqueous and comprises complexes of the active ingredient and the complex-forming polymer as described above. The aqueous solution contains about 1 to 15% by weight of the complex-forming polymer and about 2 to 30% by weight of the active ingredient based on the total weight of this emulsion. The water present in the aqueous solution comprises about 5 to 50% by wight of the final formulation. The other solution comprises the water-insoluble, film-forming polymer in an organic solvent. Suitable organic solvents include methylene chloride, ether, pentane, hexane, cyclohexane, benzene, fluorocarbons, and the like. An especially preferred organic solvent comprises chloroform ($CHCl_3$), which has a boiling point of about 61.2° C. The film-forming polymer is present in the organic solution in an amount of from about 0.1% to 20% based on the weight of the organic solvent. The aqueous and organic solutions are emulsified to produce a first emulsion. No particular order of mixing is required.

To aid in producing and stabilizing the first emulsion, a surfactant or mixture of surfactants are incorporated into one or both of the solutions before emulsification. Any surfactant which is compatible with the subject formulation is suitable in the practice of the present invention. Suitable surfactants include those available under the tradenames Tween, Span, S-Maz, Tetronic, and the like. Preferred surfactants include Tween 80, Span 80, Tetronic-704, and Tetronic-1101. It is generally preferred to add the surfactant to the organic solution before preparing the first emulsion. A preferred surfactant for preparing the first emulsion comprises a mixture of two surfactants: a fatty acid partial ester of sorbitol anhydride (e.g., sorbitan monooleate, commercially available as "Span 80" from ICI United States, Inc.) and a polyoxyethylene fatty acid ester (e.g., polyoxyethylene sorbitan monooleate, also known as polysorbate 80, commercially available as "Tween 80" from ICI United States, Inc.). The surfactant preferably comprises about 0 to 2% Tween 80, about 0 to 10% Span 80, or mixtures thereof. Most preferably the amount of surfactant is about 0.05 to 3% based on the total organic solvent in the organic solution, although the surfactant, or mixtures thereof, can be added to either the organic or the aqueous solution.

The two solutions and the surfactant are mixed, preferably with as little aeration as possible, to form a first emulsion having a continuous organic phase composed of the film-forming polymer and a discontinuous aqueous phase composed of the active ingredient-polymer complexes.

An aqueous solution comprising a suitable surfactant, the same or different from that described above, is then emulsified with the first emulsion to produce a second emulsion. A preferred surfactant for use in this step is Span 80. This aqueous solution of a surfactant preferably comprises about 0 to 15% Span 85 and/or about 0 to 8% Span 80 based on the weight of the water in this solution.

The second emulsion thus produced comprises a first discontinuous aqueous phase of the same composition as the discontinuous phase of the first emulsion, and a second discontinuous organic phase having the same composition as the continuous phase of the first emulsion, and a continuous aqueous phase. Thus, the second emulsion comprises an aqueous phase dispersed in an organic phase dispersed in an aqueous phase, thereby forming an aqueous-organic-aqueous emulsion.

The second emulsion preferably comprises, based on the total weight of this emulsion, about 0.098% to 0.3% of the complex-forming polymer, about 0.2 to 0.6% of the active ingredient, about 0.25 to 5% of the film-forming polymer, about 0.1 to 22% surfactant (or mixtures thereof), and about 10 to 15% organic solvent, with the remainder being water.

The organic solvent is removed from the second emulsion to produce an aqueous dispersion of microcapsules comprised of the film-forming polymer surrounding the aqueous cores of active ingredient-polymer complexes. The solvent can be removed by methods known in the art, such as by evaporating with heat, e.g. distillation, or under reduced pressure. To facilitate the removal of the organic solvent, it is preferred that the organic solvent have a boiling point substantially lower than that of water or of the aqueous solutions. After removal of the organic solvent the present formulations are immediately ready for use, that is, no further significant processing steps are required. The microcapsules have an approximate size distribution of from about 0.5 to about 10 microns.

Various methods known in the art can be used to alter the size of the microcapsules produced. The size of the microcapsules is inversely proportional to the amount of surfactant used. Similarly, the more vigorous or the more prolonged the emulsification, the more dispersed the first discontinuous phase, thereby resulting in smaller microcapsules.

The relative permeability of the microcapsules can also be modified. The smaller the microcapsules, the slower the release rate of the active ingredient. The use of a larger amount of the film-forming polymer will result in an increased wall thickness of the microcapsule, thereby resulting in a decreased permeability and slower release rate. Still further, the higher the boiling point of the organic solvent, the less permeable the microcapsules. It is also noted that the total amount of surfactant affects the permeability of the microcapsules. In particular, the more surfactant used, the slower the release rate.

The foregoing process is graphically depicted in FIG. 1. An aqueous active ingredient-polymer complex solution, an organic polymer solution, and a surfactant are emulsified to produce a first emulsion. This first emulsion comprises an organic continuous phase and an aqueous discontinuous phase. An aqueous solution of a surfactant is emulsified with the first emulsion to form a second emulsion. This second emulsion comprises a dispersed first discontinuous aqueous phase of the active ingredient-polymer complexes, a dispersed second discontinuous organic phase of the film-forming polymer, and a continuous aqueous phase useful as a vehicle. The organic solvent is removed to yield a liquid controlled release formulation comprising an aqueous dispersion of shells of permeable microcapsules surrounding cores of aqueous active generally ingredient-polymer complexes. The dispersions so produced are usually in the form of aqueous suspensions.

The following examples are meant to further describe the present invention and are not meant to be limiting in any manner.

EXAMPLE 1

Preparation of Liquid Controlled Release Formulation

An organic solution was prepared by mixing the following in a beaker:
 about 2 g Span 80;
 about 1 g Tween 80; and
 about 50 g chloroform.
Added to this were about 15 g Eudragit RL-100 copolymer, and the contents were stirred until the Eudragit RL-100 copolymer dissolved.

An aqueous solution was prepared by mixing the following in a beaker:
 about 0.552 g propranolol base;
 about 0.356 g Eudragit L-100 copolymer; and
 about 6.72 g absolute ethanol.
The contents were heated and stirred until all were dissolved. Then about 60 g of distilled water was slowly added to yield a slightly cloudy solution.

The organic solution and the aqueous solution were emulsified to produce a first emulsion. The emulsification was accomplished with the use of a non-aerating stirrer, such as those available from GLAS-COL Apparatus Co., Terre Haute, Ind.

In a large beaker, about 4.5 g Span 80 and about 200 g of distilled water were mixed, heated, and stirred until the Span 80 dissolved. This was combined with the first emulsion and emulsified to yield a second emulsion.

The second emulsion was heated at 65°–70° C. for approximately 20 hours to remove the chloroform.

The resulting formulation comprised an aqueous dispersion of microcapsules of Eudragit RL-100 copolymer surrounding aqueous cores of propranolol-Eudragit L-100 copolymer complexes.

Testing the Rate of Release of the Liquid Controlled Release Formulation

The testing apparatus used included a dialysis bag (Spectropor #2, 25 mm flat width) which was boiled three times in distilled water to remove any interfering substances. A 1 liter dissolution kettle was filled with USP intestinal fluid, without enzymes, and placed in a water bath at 37°±0.5° C. A USP stirrer at 100 rpm was placed in the fluid in the kettle.

An amount of the controlled release preparation made as described above was placed in the bag and the bag was then placed in the kettle.

Two flow tubes were placed in the intestinal fluid in the kettle. The rate of release of the controlled release substance, propranolol in this example, was measured by continuously pumping the intestinal fluid from the kettle into a flow cell of a UV spectrophotometer and back into the kettle.

Figure 2:
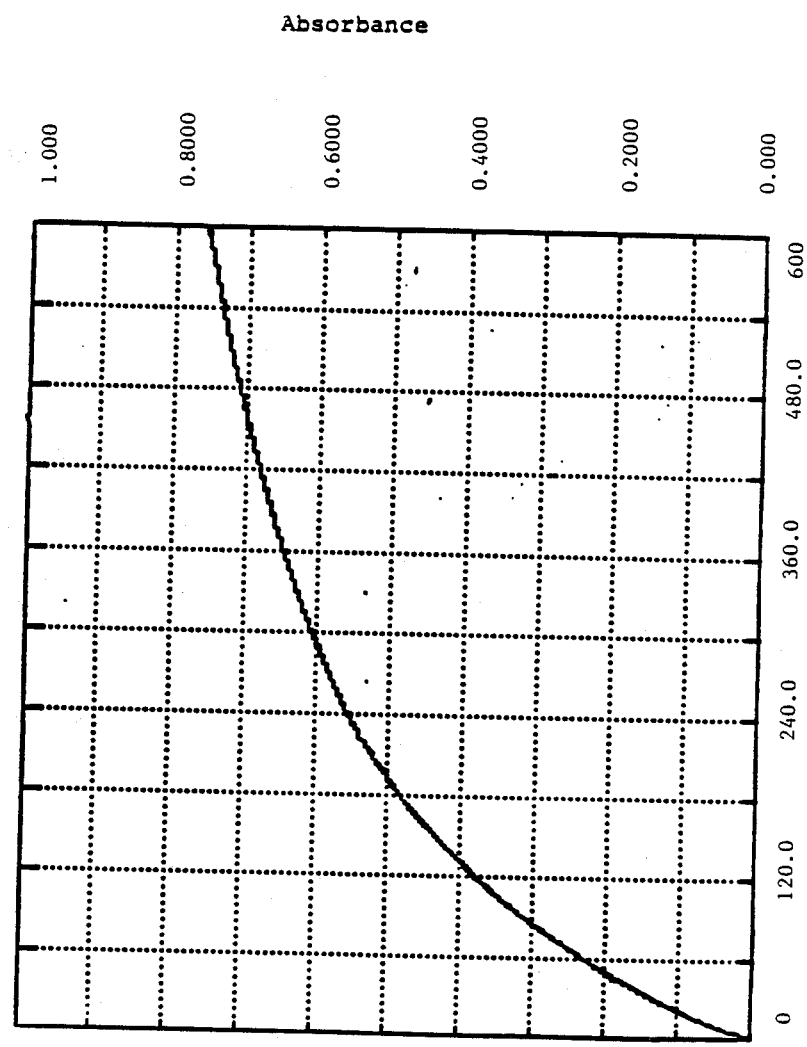
FIG. 2 is a graph showing the release characteristics of a liquid controlled release formulation of the present invention.

FIG. 2 depicts the time release curve of the concentration of propranolol in the intestinal fluid over time as measured spectophotometrically. The ordinate shows time in minutes and the abscissa depicts absorbance. The results depicted in FIG. 2 indicate a sustained release of propranolol for over ten hours (600 minutes).

EXAMPLE 2

Preparation of Liquid Controlled Release Formulation A

An organic solution was prepared by mixing:
about 2 g Span 80,
about 1 g Tween 80, and
about 50 g chloroform.

To this was added about 2.5 g Eudragit RL-100 copolymer. The solution was stirred until all the Eudragit dissolved.

An aqueous solution was prepared by mixing:
about 0.276 g propranolol base,
about 0.178 g Eudragit L-100 copolymer, and
about 3.36 g absolute ethanol.

This was heated and stirred until all ingredients were dissolved. Slowly added to this was about 30 g of distilled water to yield a slightly cloudy solution.

The organic solution and the aqueous solution were emulsified to produce a first emulsion.

About 4.5 g of Span 80 was mixed with about 200 g of distilled water. This was heated and stirred until the Span 80 dissolved and then subsequently emulsified with the first emulsion to produce a second emulsion.

The second emulsion was heated at 65°–70° C. for about 20 hours to remove the chloroform and produce an aqueous dispersion of Eudragit RL-100 copolymer permeable microcapsules surrounding aqueous cores of propranolol-Eudragit L-100 copolymer complexes.

Preparation of Comparative Liquid Release Formulation B

A solution was prepared by mixing about 0.258 g of propranolol base, about 0.176 g of Eudragit L-100 copolymer, and about 3.36 g of ethanol. This solution was stirred while being heated until all components were dissolved; a slightly cloudy solution was obtained. Then about 30 g of deionized, distilled water was slowly added to the solution.

Thus, Formulation B was an aqueous solution of a propranolol-Eudragit copolymer complexes and Formulation A was also an aqueous solution propranolol-Eudragit copolymer complexes but encapsulated in controlled release form by the method of the present invention.

Testing the Rate of Release of Formulations A and B

The same testing method used in Example 1 was used for both the encapsulated and non-encapsulated liquid formulations. The sample quantities used from each of the Formulations A and B were determined such that each sample had 40 mg of the active ingredient (propranolol). Using the amount of propranolol in each formulation and the final volume of the formulation, an amount sufficient to contain approximately 40 mg propranolol was taken from each formulation of testing.

Figure 3:
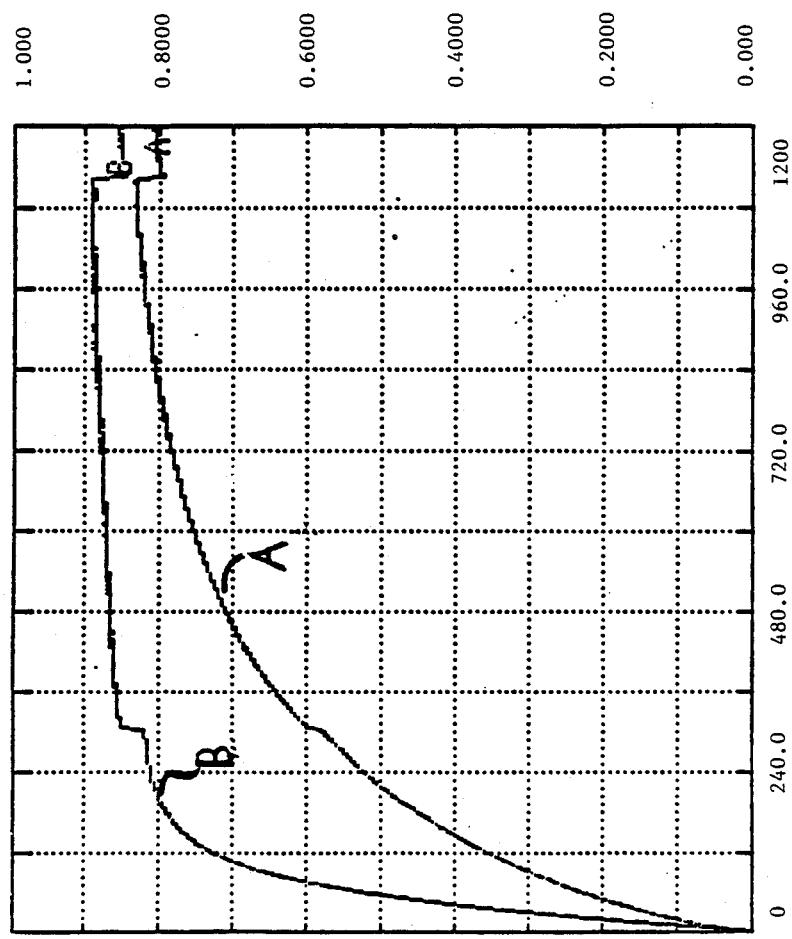
FIG. 3 is a graph which shows the release characteristics of the present controlled release formulation and of a similar formulation which is not controlled release.

FIG. 3 is a time release curve showing the release rate of the present encapsulated liquid formulation (Formulation A) over time as depicted by curve A, and the release rate of the non-encapsulated propranolol-Eudragit copolymer complex (Formulation B) depicted by curve B. As evidenced by FIG. 3, the present liquid controlled release formulation provides a virtually first order release rate over an extended period of time as compared with the non-controlled release formulation, which provides a much higher release order. Also, over 18 hours (1080 minutes), Formulation A had released 38 mg of propranolol and Formulation B had released 40 mg of the drug. Therefore, the formulations of the present invention provide a release of the active ingredient in almost the same amount as an unencapsulated complex but over a much longer period of time and at a much lower release order.

EXAMPLE 3

An organic solution was prepared by mixing:
about 2.5 g of Eudragit RL-100 copolymer,
about 4 g of Span 80,
about 0.5 g of Tween 80, and
about 5 g of chloroform.

The solution was stirred until all components were dissolved.

An aqueous solution was prepared by mixing:
about 0.276 g of chlorpheniramine base (from chlorpheniramine maleate),
about 0.178 g of Eudragit L-100 copolymer, and
about 3.36 g of absolute ethanol.

The mixture was heated and stirred until all components were dissolved. About 30 g of distilled water was then added.

The organic solution and the aqueous solution were emulsified to produce a first emulsion.

About 200 g of distilled water were mixed with about 4.58 g of Span 80 and stirred until all the surfactant was suspended in the water. This was then emulsified with the first emulsion to produce a second emulsion.

The second emulsion was heated at 65°–70° C. for approximately 20 hours to remove the chloroform and produce an aqueous suspension of chlorpheniramine in controlled release form.

EXAMPLE 4

Testing the Storage Stability of a Controlled Release Formulation

The liquid formulation produced in Example 3 was tested and then stored and tested again by the procedure used in Examples 1 and 2 in order to determine the stability of the suspension. By a manner similar to that discussed above in Example 2, a sample containing approximately 25 mg chlorpheniramine was taken from the formulation just after production and was tested. It was found after 10 hours that 18 mg of the drug had been released. The remaining formulation was stored for 32 days and then a similar sample of the formulation containing approximately 25 mg of the drug was tested. It was found after 10 hours that 19.23 mg of the drug had been released.

Figure 4A:
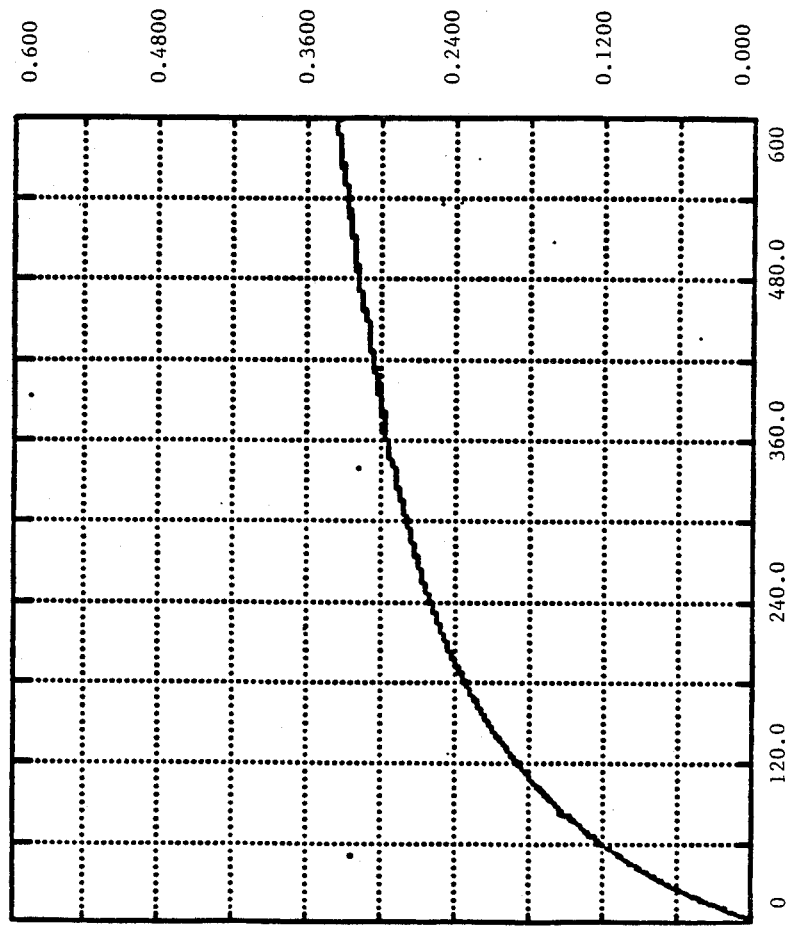
FIG. 4a depicts the release characteristics of a formulation of the present invention.
Figure 4B:
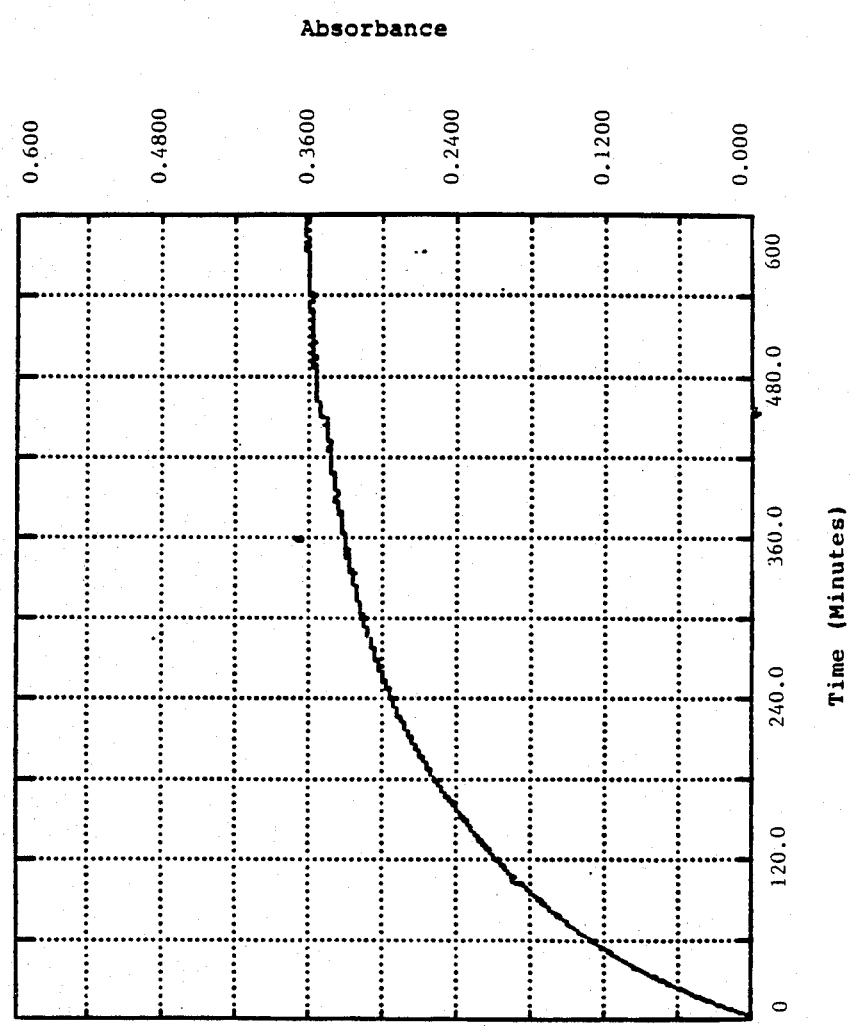
FIG. 4b depicts the release characteristics of the same formulation after 32 days of storage at ambient temperature.

These results are depicted in FIG. 4a, which shows the results of the initial test, and in FIG. 4b, which shows the results of the test after storage.

EXAMPLE 5

This example describes the production of liquid controlled release formulations of the present invention which exhibit a virtually zero order release.

Preparation of Liquid Controlled Release Formulation C

An organic solution was prepared, as by the previous examples, using:
about 2 g of Span 80,
about 1 g of Tween 80,
about 50 g of chloroform, and
about 15 g of Eudragit RL-100 copolymer.

An aqueous solution was prepared using:
about 0.276 g propranolol base,
about 0.176 g Eudragit L-100 copolymer,
about 3.36 g ethanol, and
about 30 g distilled water.

The aqueous and organic solutions were emulsified. An aqueous solution of about 4.5 g Span 80 in 200 g of water was emulsified with the first emulsion to produce a second emulsion. The second emulsion was heated to 65°-70° C. for approximately 20 hours to produce the final Formulation C.

Preparation of Liquid Controlled Release Formulation D

An organic solution was prepared using:
about 8 g of Span 80,
about 1 g of Tween 80,
about 50 g of chloroform,
about 7.5 g of Eudragit RL-100 copolymer, and
about 2.5 g of Eudragit RS-100 copolymer.
An aqueous solution was prepared using:
about 0.276 g of propranolol base,
about 0.178 g of Eudragit L-100 copolymer,
about 3.36 g of ethanol, and
about 30 g of distilled water.

These two solutions were emulsified. An aqueous solution including about 8.5 g of Span 80 and about 16.5 g of Span 85 in about 200 g of water was emulsified with the first emulsion. The final emulsion was heated for approximately 20 hours at 65°-70° C. to evaporate the chloroform.

Preparation of Liquid Controlled Release Formulation E

An organic solution was prepared having the following components:
about 8 g of Span 80;
about 1 g of Tween 80;
about 50 g of chloroform; and
about 10 g of Eudragit RL-100 copolymer.
An aqueous solution was prepared with the following:
about 3.45 g of propranolol base;
about 2.25 g of Eudragit L-100 copolymer;
about 42 g of ethanol; and
about 375 g of distilled water.

The organic solution and about 31.5 g of the aqueous stock solution were emulsified, an aqueous solution of:
about 8.5 g of Span 80 and
about 16.5 g of Span 85 in
about 200 g of distilled water
was added, and the emulsion was emulsified again. The final emulsion was heated at 65°-70° C. for approximately 20 hours.

Formulation D had a slower release rate than Formulation C due to the use of Eudragit RS-100 copolymer as the film-forming polymer as opposed to Eudragit RL-100 copolymer, and also because Formulation D had a greater total amount of surfactant. Formulation E had a slower release rate than Formulation C due to the much larger amount of surfactant used, even though a lesser amount of Eudragit RL-100 copolymer was used as the film-forming polymer.

Testing

Using the testing procedure described above, a volume sample comprising about 40 mg of propranolol was taken from each of the three formulations and separately tested. After 20 hours, the following amounts of the drug were released from each sample:

| Formulation C | 37 mg |
| Formulation D | 18 mg |
| Formulation E | 8 mg |

Figure 5A:
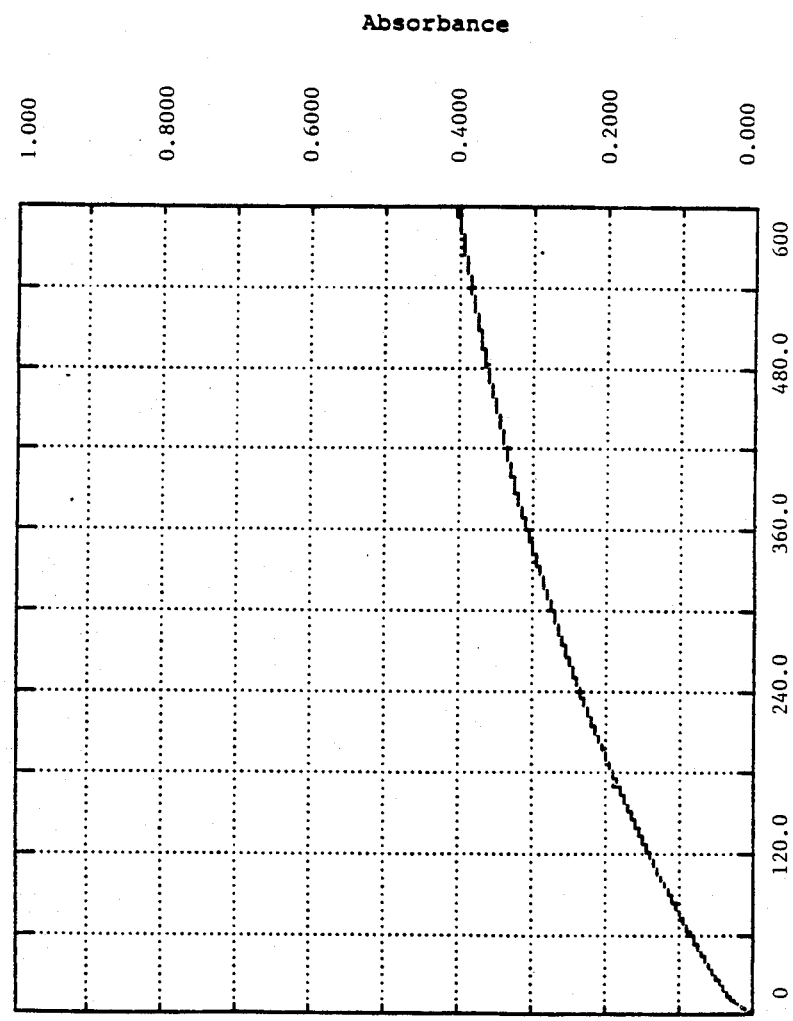
FIGS. 5a and 5b depict release characteristics of formulations comprising a mixture of microcapsules prepared using different polymers which provide close to zero-order release rate.

Next, samples of Formulation C and of Formulation D were mixed and subject to the same testing procedure. These samples were selected such that the mixture comprised a total of 40 mg of propranolol. The results of this test are depicted in FIG. 5a. As seen in FIG. 5a, this mixture exhibits a release order less than any of the single formulations tested before. This mixture is closer to a zero order release than any of the above examples.

Figure 5B:
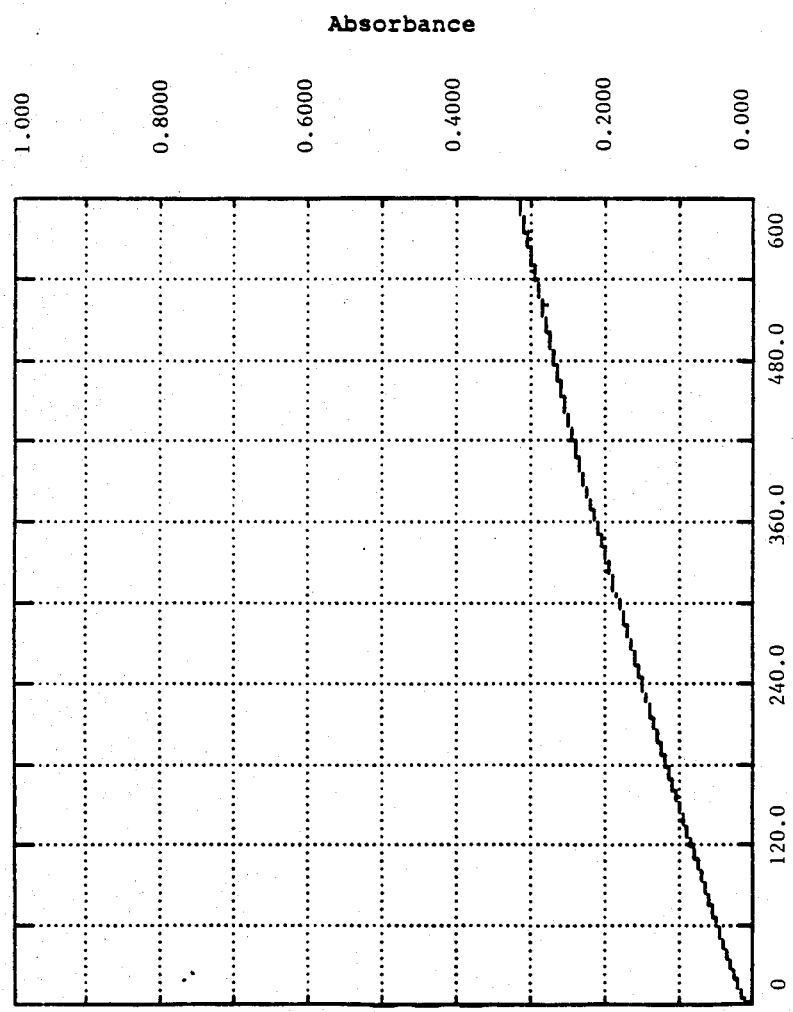

Finally, samples of Formulation C and Formulation E, each comprising 20 mg of propranolol, were mixed and subjected to testing. These results are shown in FIG. 5b, which depicts a time release curve showing a release order close to zero.

The results of this example thus show that mixtures of the formulations of the present invention can be utilized to obtain specific release characteristics. Furthermore, different combinations of formulations having different release characteristics may be used to achieve constant release orders and varying release orders.

EXAMPLE 6

Preparation of Liquid Controlled Release Formulation

An aqueous solution was prepared by mixing the following:
about 0.25 g indomethacin,
about 0.25 g Eudragit E-100 copolymer, and
about 6 g absolute ethanol These components were heated and stirred until all of the components were dissolved. A solution containing about 30 g distilled water and about 3 g absolute ethanol was then mixed with the solution to yield a light yellow, slightly cloudy solution.

An organic solution was prepared by mixing the following components until all were dissolved:
about 2 g of Span 80,
about 1 g of Tween 80,
about 50 g of chloroform, and
about 1 g of Eudragit RL-100 copolymer.

The organic and aqueous solutions were emulsified to produce a first emulsion. An aqueous solution of about 4.5 g Span 80 in about 200 g distilled water was heated and stirred until all of the surfactant dissolved, and was then emulsified with the first emulsion to produce a second emulsion.

The second emulsion was heated at about 65°-70° C. for approximately 20 hours to remove the chloroform and produce an aqueous dispersion of Eudragit RL-100 copolymer permeable microcapsules surrounding aqueous cores of indomethacin-Eudragit E-100 copolymer complexes.

Testing the Rate of Release of the Liquid Controlled Release Formulation

Using a procedure similar to that described in Example 1, two volume samples of the final suspension, each containing about 50 mg of indomethacin, were tested. For one sample, after about 10 hours approximately 26.4 mg of the indomethacin had been released. For the other sample, the following results were obtained:

| time (hours) | total amount of drug released |
|---|---|
| 15 | 34.9 mg |
| 22 | 38.1 mg |
| 30 | 39.1 mg |
| 45 | 40.7 mg |

Thus, inter alia, this example shows the microencapsulation of an acidic active ingredient complexed with a polymer and its subsequent transformation into a liquid controlled release formulation.

The foregoing descriptions and embodiments are meant to be illustrative and exemplary and in no manner limiting. The various modifications and changes to the present invention apparent to those of ordinary skill in the art are intended to be within the scope and spirit of the present invention as defined herein.

What is claimed is:

1. A method for preparing a liquid controlled release dosage formulation, comprising the steps of:
   preparing an aqueous solution of an active ingredient and a complex-forming polymer to produce active ingredient-polymer complexes;
   preparing an organic solution of a film-forming polymer in an organic solvent;
   adding a first surfactant to said aqueous solution of to said organic solution or to both solutions;
   emulsifying said solutions to produce an aqueous-organic first emulsion;
   preparing an aqueous solution of a second surfactant;
   emulsifying said aqueous solution of said second surfactant with said first emulsion to produce an aqueous-organic-aqueous second emulsion; and
   removing said organic solvent from the second emulsion to produce an aqueous dispersion of microcapsules each having a permeable polymeric shell of said film-forming polymer encapsulating an aqueous core of active ingredient-polymer complexes.

2. The method as defined in claim 1 further comprising the step of adding a second aqueous solution of active ingredient-polymer complexes to said emulsifying step which produces the first emulsion.

3. The method as defined in claim 1 wherein said active ingredient is selected from the group consisting of pharmaceuticals, vitamins, minerals, and hormones, or mixtures thereof, which are capable of forming complexes in aqueous solution.

4. The method as defined in claim 1 wherein said active ingredient is chlorpheniramine.

5. The method as defined in claim 1 wherein said active ingredient is propranolol.

6. The method as defined in claim 1 wherein said organic solvent is chloroform.

7. The method as defined in claim 1 wherein said film-forming polymer comprises a copolymer of acrylic and methacrylic acid esters having pendant quaternary ammonium groups.

8. The method as defined in claim 1 wherein said complex-forming polymer comprises a copolymer of acrylic and methacrylic acid esters having free acid groups.

9. The method as defined by claim 1 wherein said complex-forming polymer comprises a cationic copolymer of dimethylaminoethyl methacrylates and neutral methacrylic acid esters.

10. The method as defined in claim 1 wherein said organic solvent is removed by heating.

11. The method as defined in claim 1 wherein said first surfactant is added to said organic solution.

12. The method as defined in claim 1 wherein said first or said second surfactant, or both surfactants, comprises fatty acid partial esters of sorbitol anhydride.

13. A liquid controlled release formulation produced by the method of claim 1.

14. A liquid controlled release formulation comprising a mixture of microcapsular dispersions each produced by the method of claim 1.

15. The liquid controlled release formulation as defined in claim 14 wherein each of said microcapsular dispersions comprises a different active ingredient.

16. The liquid controlled release formulation as defined in claim 14 wherein the microcapsules of each dispersion have different release characteristics.

17. A method for producing a liquid controlled release formulation, comprising mixing at least two microcapsular dispersions each produced by the process of claim 1.

18. A method for preparing a liquid controlled release formulation, comprising the steps of:
   preparing an aqueous solution of about 2 to 30 wt.% of an active ingredient and about 1 to 15 wt.% of a complex-forming polymer to produce active ingredient-polymer complexes, said amounts based on the aqueous solution;
   preparing an organic solution of about 0.1 to 20 wt.% of a film-forming polymer in an organic solvent, said amount based on the organic solution;
   adding about 0.05 to 3 wt.% of a first surfactant to said aqueous solution or to said organic solution or to both solutions, said amount based on said organic solvent;
   emulsifying said solutions to produce an aqueous-organic first emulsion;
   preparing an aqueous solution of about 0 to 23 wt.% of a second surfactant, said amount based on the water present in this solution;
   emulsifying said aqueous solution of said second surfactant with said first emulsion to produce an aqueous-organic-aqueous second emulsion; and
   removing said organic solvent to produce an aqueous dispersion of microcapsules, each having a permeable polymeric shell of said film-forming polymer encapsulating an aqueous core of active ingredient-polymer complexes.

19. The method as defined by claim 18, wherein said organic solvent comprises about 10 to 15 wt.% of said second emulsion.

20. A product produced by the method of claim 18 comprising: about 0.25 to 5 wt.% of said film-forming polymer; about 0.098 to 0.30 wt.% of said complex-forming polymer; and about 0.1 to 22 wt.% of said surfactants combined, said amounts based on the final aqueous dispersion product.

* * * * *